(12) United States Patent
Steffen

(10) Patent No.: US 9,586,005 B2
(45) Date of Patent: Mar. 7, 2017

(54) DUAL SYRINGE DELIVERY DEVICE AND METHOD OF USE

(71) Applicant: Dennis L Steffen, Tavernier, FL (US)

(72) Inventor: Dennis L Steffen, Tavernier, FL (US)

( * ) Notice: Subject to any disclaimer, the term of this patent is extended or adjusted under 35 U.S.C. 154(b) by 583 days.

(21) Appl. No.: 14/042,574

(22) Filed: Sep. 30, 2013

(65) Prior Publication Data

US 2015/0094689 A1 Apr. 2, 2015

(51) Int. Cl.
| | |
|---|---|
| *A61M 5/19* | (2006.01) |
| *A61B 17/00* | (2006.01) |
| *A61M 5/315* | (2006.01) |
| *A61M 3/00* | (2006.01) |
| *A61C 5/06* | (2006.01) |
| *A61M 5/31* | (2006.01) |

(52) U.S. Cl.
CPC ......... *A61M 5/19* (2013.01); *A61B 17/00491* (2013.01); *A61C 5/062* (2013.01); *A61C 5/064* (2013.01); *A61C 5/068* (2013.01); *A61M 3/005* (2013.01); *A61M 5/315* (2013.01); *A61B 2017/00495* (2013.01); *A61M 5/3137* (2013.01); *A61M 5/31511* (2013.01)

(58) Field of Classification Search
CPC .............. A61M 5/19; A61M 3/005; A61B 2017/00495; A61C 5/062; A61C 5/064; A61C 5/068

USPC ..................................................... 604/82, 191
See application file for complete search history.

(56) References Cited

U.S. PATENT DOCUMENTS

| | | | |
|---|---|---|---|
| 3,563,240 A | 2/1971 | Silver | |
| 4,359,049 A * | 11/1982 | Redl | A61B 17/00491 604/191 |
| 4,631,055 A | 12/1986 | Redl | |
| 5,368,563 A | 11/1994 | Lonneman | |
| 6,394,982 B1 | 5/2002 | Ehrefels | |
| 6,454,739 B1 | 9/2002 | Chang | |
| 6,458,095 B1 | 10/2002 | Wirt | |
| 6,461,325 B1 | 10/2002 | Delmotte | |
| 6,610,033 B1 * | 8/2003 | Melanson | A61B 17/00491 604/181 |
| 6,716,195 B2 | 4/2004 | Nolan | |
| 6,783,514 B2 | 8/2004 | Tovey | |
| 7,037,289 B2 | 5/2006 | Dodge | |
| 7,468,049 B2 | 12/2008 | Laveault | |
| 7,883,501 B2 | 2/2011 | McIntosh | |
| 7,959,612 B2 | 6/2011 | Thompson et al. | |
| 2003/0055384 A1 | 3/2003 | Enrefels | |
| 2006/0116646 A1 | 6/2006 | Weiss | |
| 2008/0275403 A1 | 11/2008 | Maskamp | |
| 2013/0331771 A1 * | 12/2013 | Kirk | A61M 35/003 604/24 |

* cited by examiner

*Primary Examiner* — Laura Bouchelle
*Assistant Examiner* — Anh Bui

(57) ABSTRACT

The present invention relates to a dual syringe delivery device consisting of three components which when collectively assembled result in the capability of accommodating varying syringe volume sizes.

19 Claims, 11 Drawing Sheets

SECTION 1-1

DUAL SYRINGE DELIVERY DEVICE AND METHOD OF USE

FIELD OF THE INVENTION

The present invention relates to a dual, syringe delivery device and method of use. Although the invention may be adapted to uses other then described within this application the following description of the invention pertains to usage with an atomizer spray head and method for the application of the two components of fibrin glues. Fibrin glue (also called fibrin sealant) is a formulation used to create a fibrin clot. It is made up of fibrinogen (lyophilized pooled human concentrate) and thrombin (bovine, which is re-constituted with calcium chloride) that are applied to the tissue sites to glue them together. Thrombin is an enzyme and converts fibrinogen into fibrin monomers between 10 and 60 seconds giving rise to a three dimensional gel.

INTRODUCTION

Conventional dual syringe devices associated with atomizer spray heads and two part fibrin glue work by delivering the two components of fibrin glues which is pre-loaded Into syringes and dispersed through an atomizer spray head, the fibrin is usually a two part solution which becomes active when combined. Since the cost of the fibrin glues is a major factor it is usually used in the precise amount needed for the procedure this is why the Dual Syringe Delivery Device described in this application is especially useful with applications relating to the delivery of fibrin glue. It enables application to be applied using a variety of syringe volume sizes e.g. 1 ml, 2 ml, 5 ml as described herein with just one system, unlike present units which require specific sized delivery systems to match the different syringe volume sizes. The invention describe in this application illustrates how different syringe volume sizes can be accommodated by the Dual Syringe Delivery Device.

BRIEF DESCRIPTION

The present invention relates to a dual syringe delivery device consisting of three components which when collectively assembled result in a device with capability of accommodating syringe volume sizes from 1 ml through 5 ml. There exist many techniques for the application of fibrin glues with dual syringe devices. Application of the two compounds which make up fibrin glues can be accomplished in a number of ways. In one method, the admixture is drawn into a single syringe and ejected via an appropriate sized needle. In another method a dual syringe device is used which snaps into a holder and plunger system then held to the atomizer spray head by a lanyard; this system requires a size matching holder, plunger, and lanyard configuration for each varying syringe volume. Other conventional techniques employ large and size restricted configuration which directly affects the cost of a procedure which requires the use of fibrin glue. Additionally, a number of special applicators are commercially available. Although the example of the use of this invention focuses on fibrin glues it should not be construed as limited to only such application.

In one embodiment, the invention utilizes a dual syringe delivery device configured with an atomizer spray head.

In another embodiment, the invention utilizes a dual syringe delivery device configured with dual inlet hypodermic needle manifold capable of accommodating an industry standard hypodermic needle capable of delivering a two part drug.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Figure 1:
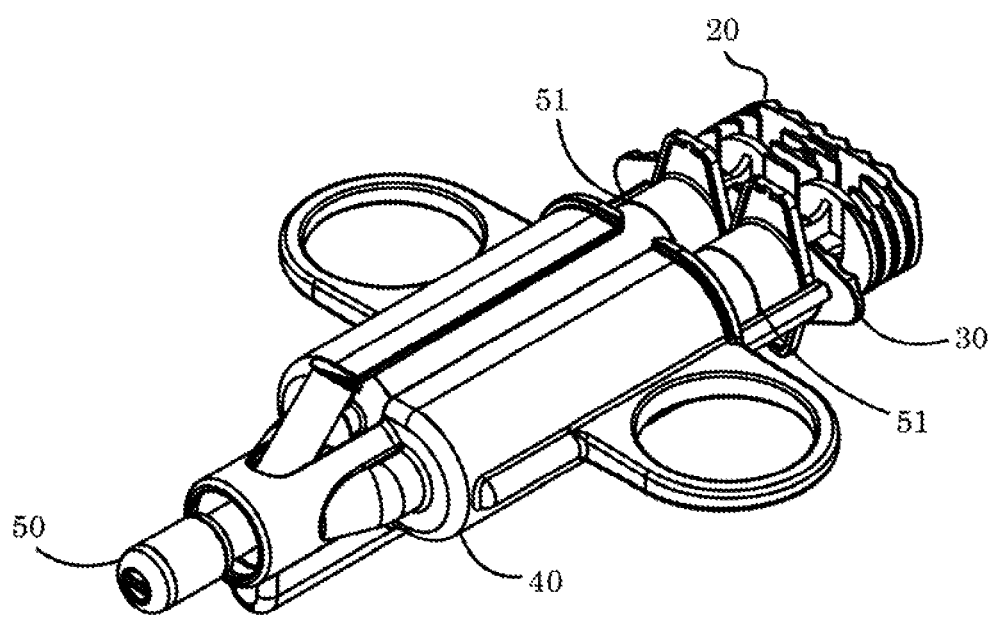
FIG. 1 is an isometric view of the primary components in the dual syringe delivery device; the configuration illustrates the application with dual syringes and an atomizer spray head, all in accordance with the invention.

A dual syringe delivery device for the application of the two components of fibrin glues embodying the principles of the invention is provided. The device comprises a cradle, plunger, and holster.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of" The use of "consisting essentially of" means, e.g., that a method may include additional steps, but only if the additional steps do not materially alter the basic and novel characteristics of the claimed method. Unless specified or limited otherwise, the terms "joined", "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references slates what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content, clearly dictates otherwise.

Unless otherwise noted, technical terms are used according to conventional usage. However, as used herein, the following definitions may be useful in aiding the skilled practitioner in understanding the invention. Such definitions shall be applied, unless a different definition, is given in the claims or elsewhere in this specification.

In view of the foregoing disadvantages inherent in conventional dual syringe fibrin glue application systems, the invention provides a novel device and method for application of fibrin glues. Given that many dual syringe fibrin glue delivery devices are capable of accommodating only single sized syringes. The invention provides a unique and cost effective method for the delivery of fibrin glues.

The full advantage of the dual syringe delivery device pertains to its ability to easily handle a range of syringe sizes with one configuration; additionally the ease of use and simplicity of the design makes it a superior option over current delivery systems. It should also be noted that during the surgical act of applying the fibrin glue to the desired area, time is always and an issue and this invention directly addresses that issue. In accordance with the invention, a surgeon is able to avoid undue wasted time attempting to assemble/load current system or match the syringe size to the system.

Figure 2:
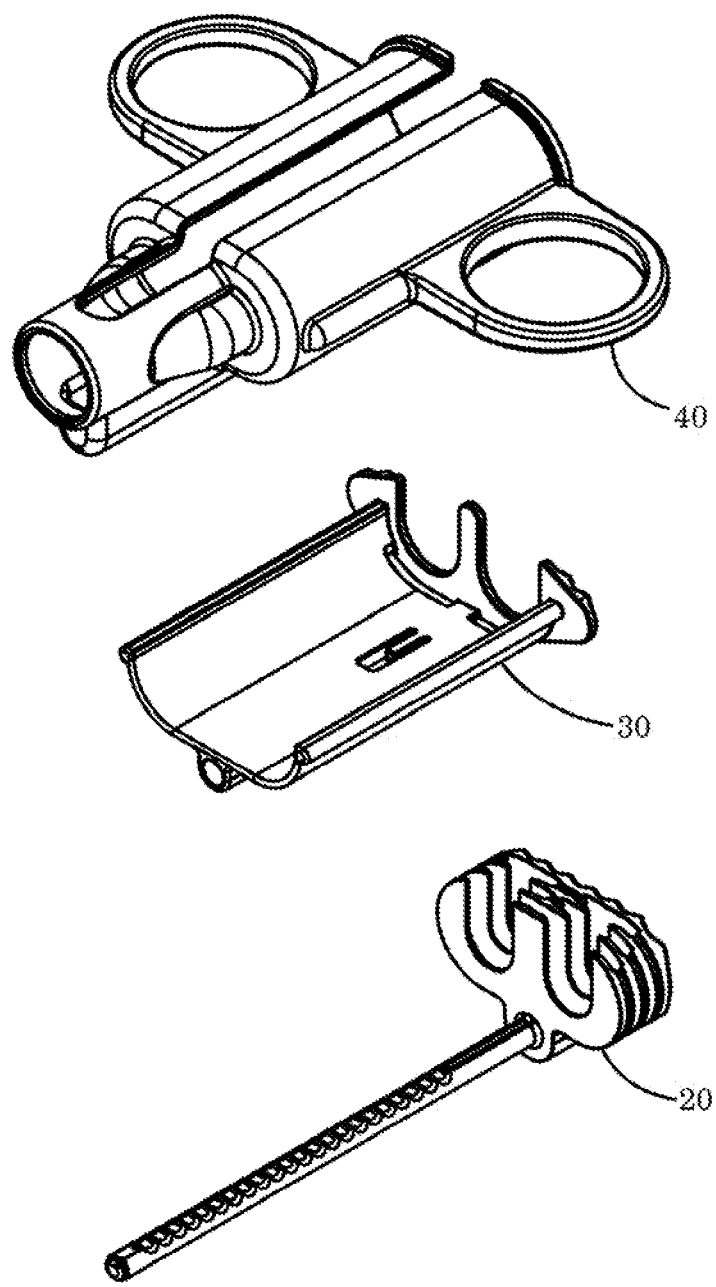
FIG. 2 is an isometric view of each of the three primary components of the dual syringe delivery device, all in accordance with the invention.

Reference is now made to FIGS. 1-11 in which a Dual Syringe Delivery Device, generally designated by reference numeral 10, in accordance with the invention is shown. Device 10 collectively comprised of a plunger 20, a cradle 30 and a holster 40 for delivery of fibrin glues. In an illustrated embodiment, FIG. 1 the final, configuration of the plunger 20, cradle 30, holster 40, dual 5 ml syringes 51, and atomizer spray head 50 is defined. Additionally illustrated in FIG. 2 are the principle components, plunger 20, cradle 30, and holster 40 which make up the system. A typical atomizer spray head, connects to two solution sources e.g. syringes and one air/gas source e.g. low pressure compressed air. The holster 40 is configured for this application but can optionally be configured in other manners and not limited to this configuration.

Figure 3:
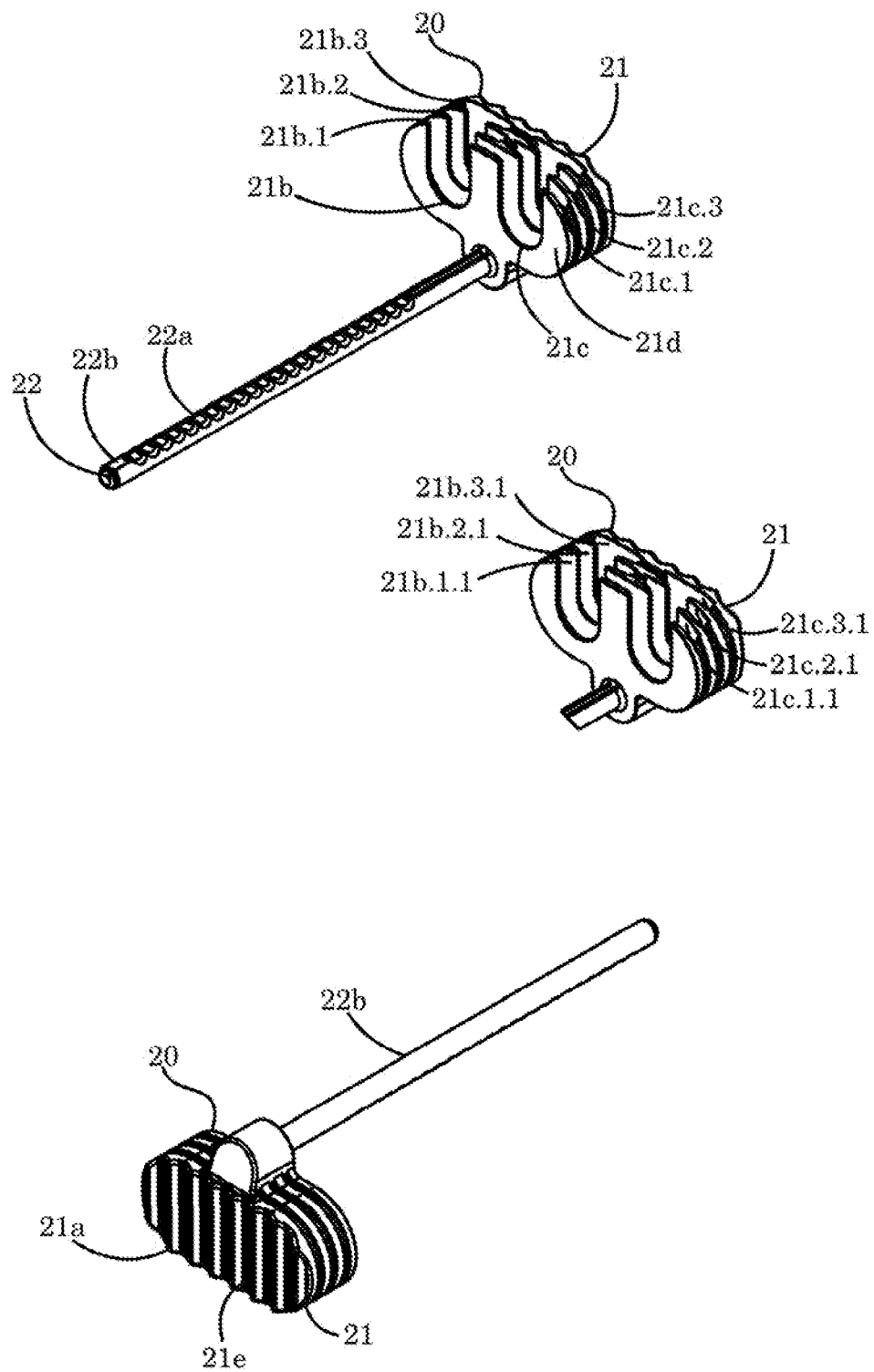
FIG. 3 is an isometric view of the plunger component of the dual syringe delivery device, all in accordance with the invention.

As shown in FIG. 3, the plunger 20 is comprised of a head 21 obround in shape having a distal surface 21$d$ and a proximal surface 21$e$, and having a shaft 22 cylindrical in shape and joined to the head at the distal surface 21$d$. The head 21 has a set of U shaped slots 21$b$ and 21$c$ extending from the distal surface 21$d$ to surfaces 21$b$.3.1 and 21$c$.3.1 and being proportioned to allow passage of the syringe 51 plunger shaft 51$a$, additionally there are three sets of horizontal slots either side of the longitudinal centerline which are spaced and proportioned to accommodate the varying syringe plunge head 51$b$ sizes and syringe plunger 51$a$ stroke, one side 21$b$.1, 21$b$.2, 21$b$.3, and opposite 21$c$.1, 21$c$.2, 21$c$.3 proportioned to allow passage of the syringe 51 plunger shaft head 51$b$, e.g. slots 21$b$.1 and 21$c$.1 which are proportion for a 5 ml syringe plunger head and positioned to allow the full stroke of the 5 ml syringe plunger stroke. In addition each horizontal slot has an upper surface 21$b$.1.1, 21$b$.2.1, 21$b$.3.1 and 21$c$.1.1, 21$c$.2.1, 21$c$.3.1 which contacts the top surface the syringe plunger shaft head 51$b$. The plunger 20 head 21 has a series of protrusion 21$a$ on the proximal surface 21$e$ to provide grip when the plunger is depressed during usage. The shaft 22 which is joined to the head 21 has a concave surface 22$b$ to prevent rotation when inserted into aperture 33$b$ and joined with the convex surface 33$c$ of the cradle 30, and which faces in the direction of the slots 21$b$ and 21$c$ and extending from the most distal tip of the shaft 22 to surface 21$d$ of the head 21, also a series of grooves 22$a$ lying perpendicular to the longitudinal centerline and which face in the direction of the slots 21$b$ and 21$c$ on the head 21, the opposite surface of the shaft 22$b$ is smooth and convex. The grooves 22$a$ which come into contact with the detent tab 34 and pawl 34$a$ located on the cradle 30 when the shaft 22 is inserted into the aperture 33$b$ on the cradle 30. The grooves 22$a$ and detent tab 34 and pawl 34$a$ join to create a static positioning element to hold the plunger 20 in position relative to the cradle 30 to facilitate loading the syringe and atomizer spray head configuration 10.1.

Figure 4:
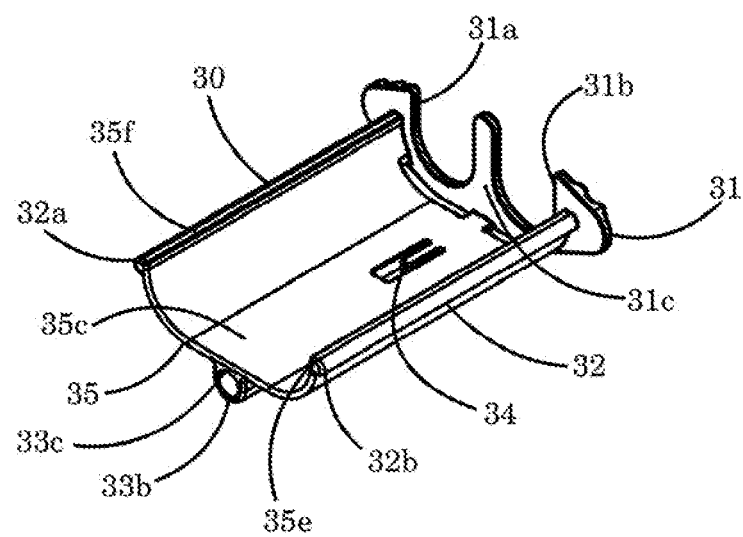
FIG. 4 is an isometric view of the cradle component of the dual syringe delivery device, all in accordance with the invention.
Figure 4:
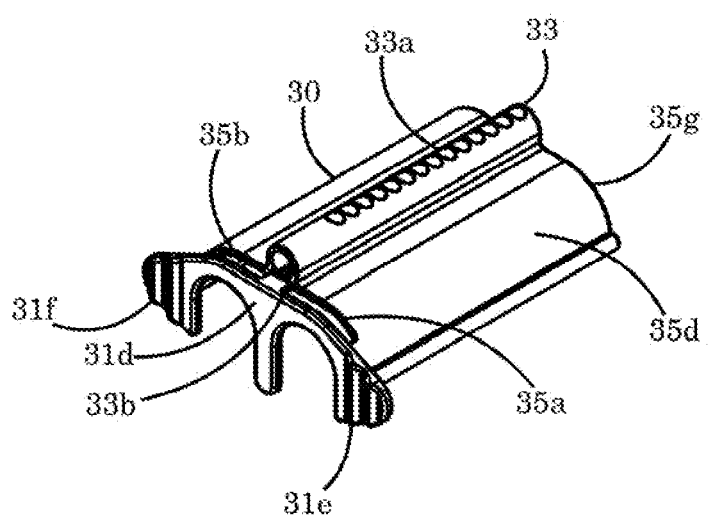

As shown in FIG. 4, the cradle 30 comprised of a proximal flange 31 having a distal surface 31$c$ and a proximal surface 31$d$ which extends equally about the longitudinal centerline and is joined to a semi-obround body portion 35 having an interior surface 35$c$ and an exterior surface 35$d$ which extends distally with the outer edges extending equally about the longitudinal centerline and terminating at the longitudinal center plane. The proximal flange 31 has two U shaped slots 31$a$ and 31$b$ located either side of the longitudinal center-line extending from the distal surface 31$c$ to the proximal surface 31$b$ and proportioned to allow passage of the syringe 51 plunger shaft 51$a$, correspondently the body 35 has two apertures 35$a$ and 35$b$ extending from the interior surface 35$c$ to the exterior surface 35$d$ and positioned-against the flange distal surface 31$c$ and adjacent to the U shaped slots 31$a$ and 31$b$ located on the flange 31 and being proportioned to allow passage of the syringe 51 finger tab 51$c$. The flange 31 has raised elements 31$e$ and 31$f$ on the proximal surface 31$d$ located at its outer extent about the longitudinal centerline. The body 35 has a tubular protrusion 33 located on the and joined to the exterior surface 35d and centered on the longitudinal centerline and extends from the most distal edge 35g of the body to the proximal end terminating parallel to the distal edges of the two apertures 35a and 35b, the tubular protrusion 33 has an aperture 33b which extends the length of the protrusion and which is proportioned to allow insertion of the shaft 22 of the plunger 20. In addition the tubular protrusion 33 has a series of grooves 33a lying perpendicular to the longitudinal centerline and facing in the direction opposite the body 35. The grooves 33a come into contact with the detent tab 42 and pawl 42a located on the holster 40 when the cradle 20 is inserted into the holster 40. The grooves 33a and detent tab 42 and pawl 42a join to create a static positioning element to hold the cradle 30 in position relative to the holster 40 once the; cradle, plunger, dual syringe and atomizer spray head configuration 10.3 are inserted in the holster. A rail set 32 having a first rail 32a located on the outer extent of the body 35f and having a second rail 32b located on the outer extent of the body 35e which extend from the most distal edge 35g of the body 35 to the base of the distal surface 31c of the flange 31 and are proportioned to slide within the channels 46a and 46b located on the body 46 of the holster 40 when, the two components are joined.

Figure 5:
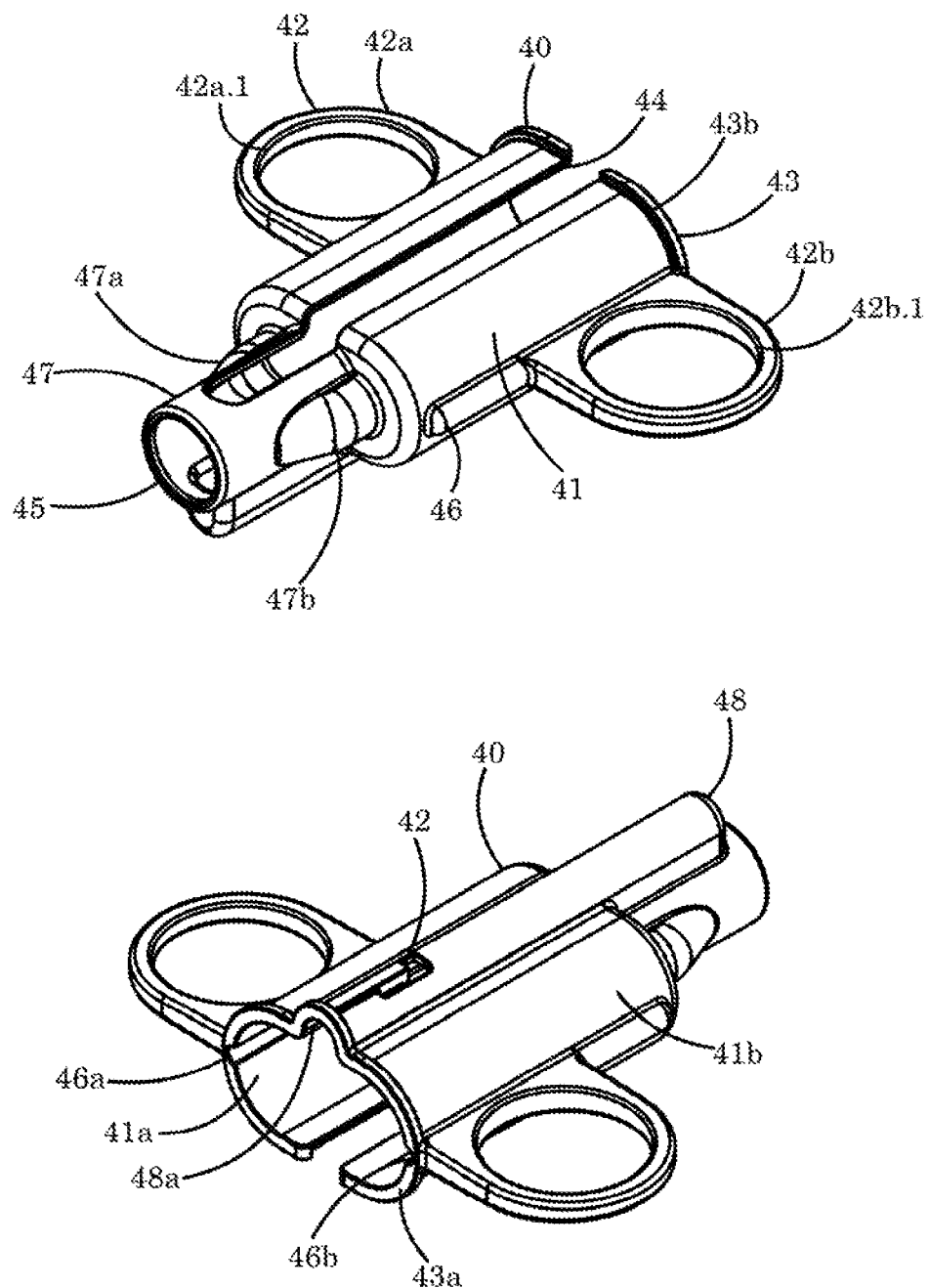
FIG. 5 is an isometric view of the holster component of the dual syringe delivery device, all in accordance with the invention.

As shown in FIG. 5, the holster 40 comprised of a proximal flange 43 having a distal surface 43b and a proximal surface 43a which extends the perimeter of the body 41 and is flush to the interior surface of the body 41 a and overhangs the exterior surface 41b of the body 41 the flange provides added rigidity to the body walls, the body 41 that extends distally has an interior surface 41a and an exterior surface 41b, and distal nose area 47. A dual finger loop 42 having a first loop 42a and a second loop 42b located on and joined to the exterior surface 41b of the body 41 extending distally and laterally equally about the longitudinal centerline and the longitudinal center plane and is proximally joined to the flange 43. The proximal flange 43 is interrupted equally either side of the longitudinal centerline by an aperture 44 which extends distally and which is proportioned to allow passage of the atomizer spray head 50 air source fitting 50a. The dual finger loops 42a and 42b have apertures 42a.1 and 42b.1 proportioned to allow passage of an average sized human hand index finger and middle finger for gripping the device during usage. The distal nose area of the body 47 has an aperture 45 in the most distal tip which is proportioned to allow passage the spray head tip 50c also in the distal nose area 47 are two contours 47a and 47b which mirror the contours 50b of the atomizer spray head, the contours 47a and 47b act as a physical stop against the spray head when the device is fully assembled with the spray head 50 seated in the device. Located on the inner surface 41a of the body 41 and opposite the aperture 44 is a U shaped channel 48 centered on the longitudinal centerline which extends from the most proximal surface 43a on the flange 43 distally to the distal nose area 47 located along this channel is a retention tab 42 with pawl 42a which joins with the grooves 33a on the cradle 30 as previously described. Along the inner surface 41a of the body 41 a set of U shaped channels 46a and 46b centered on the longitudinal center plane and which extend from the most proximal surface 43a on the flange 43 distally along the length of the body 41. The U shaped channels are proportioned to allow passage of the rail set 32 located on the outer extent of the cradle body 35 as previously described when the two components are joined.

Figure 6:
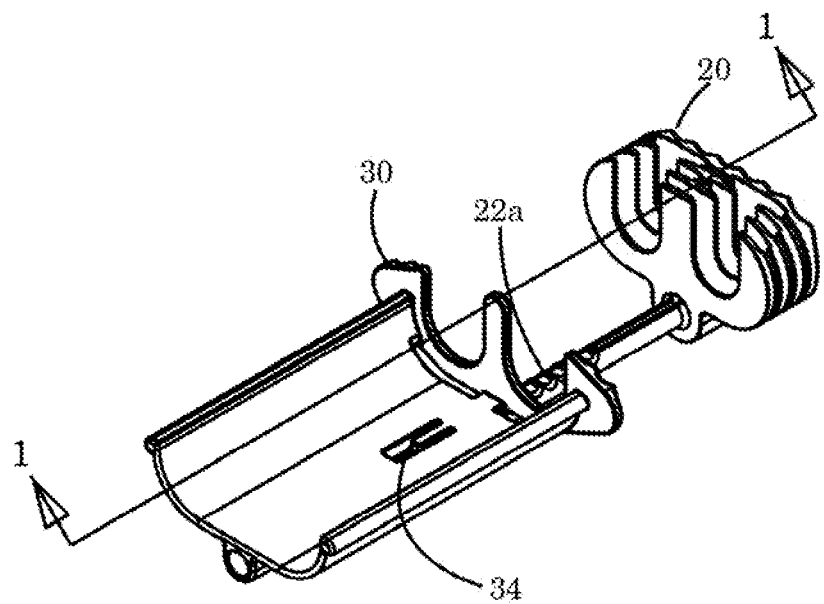
FIG. 6 is an isometric view and a longitudinal cross section of the plunger and cradle components as they would be configured in normal usage of the dual syringe delivery device, all in accordance with the invention.
Figure 6:
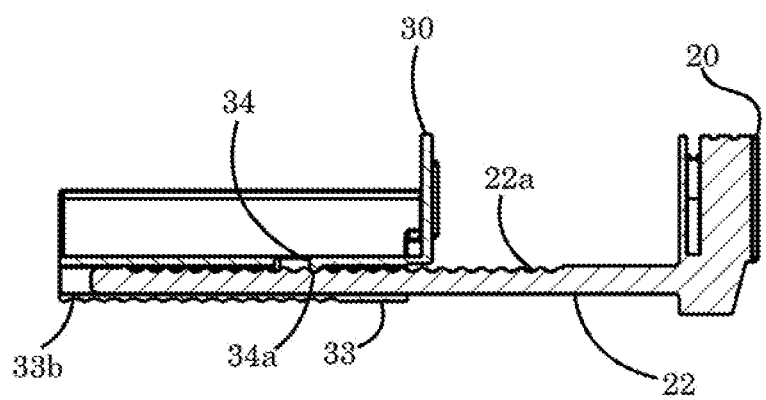

As shown in FIG. 6, the longitudinal centerline cross section 1-1 of the plunger 20 and cradle 30 as they would be joined together in normal use serve to further illustrate the relationship between component elements. The cross section further helps clarify the relationship of the retaining tab 34 and pawl 34a of the cradle 30 to the grooves 22a of the shaft 22 on the plunger 20; additionally it illustrates the shaft 22 of the plunger 20 as it is positioned in the aperture 33b of the cradle 30.

Figure 7:
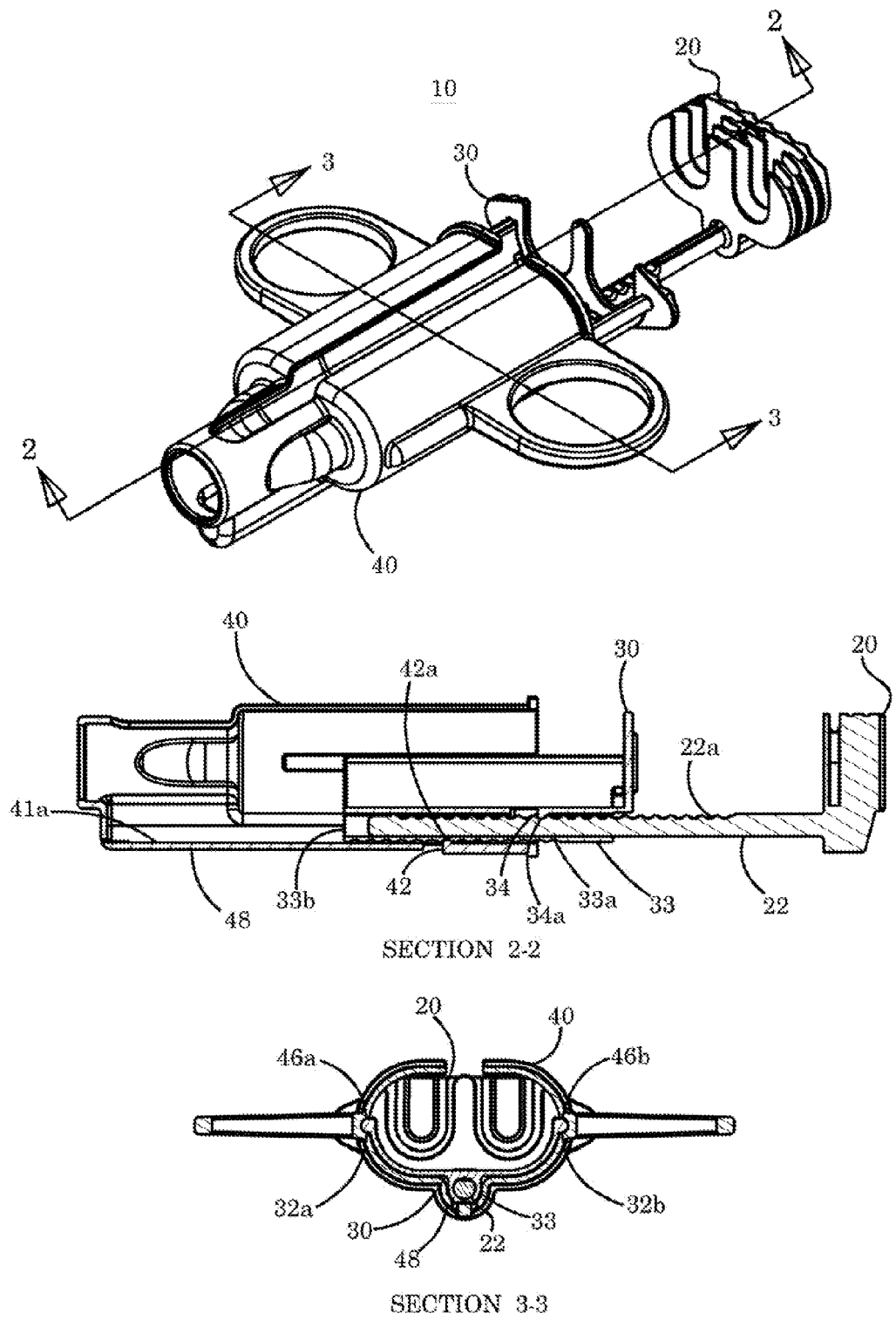
FIG. 7 is an isometric view, longitudinal and lateral cross sections, of the plunger, cradle and holster components as they would be configured in normal usage of the dual syringe delivery device, all in accordance with the invention.

As shown in FIG. 7, the longitudinal, centerline cross section 2-2 and the lateral cross section 3-3 of the plunger 20, cradle 30 and holster 40 as they would be joined together in normal use serve to further illustrate the relationship between component elements. The longitudinal cross section 2-2 further clarifies the relationship of the retaining tab 42 and pawl 42a of the holster 40 to the grooves 33a of the cradle 30. The lateral cross section 3-3 further clarifies the relationship of the side rails 32a and 32b of the cradle 30 and how they interface with the channels 46a and 46b of the holster 40; additionally it illustrates the interface between the U shaped protrusion 33 of the cradle 30 as it is positioned in the U shaped channel 48 of the holster 40.

Figure 8:
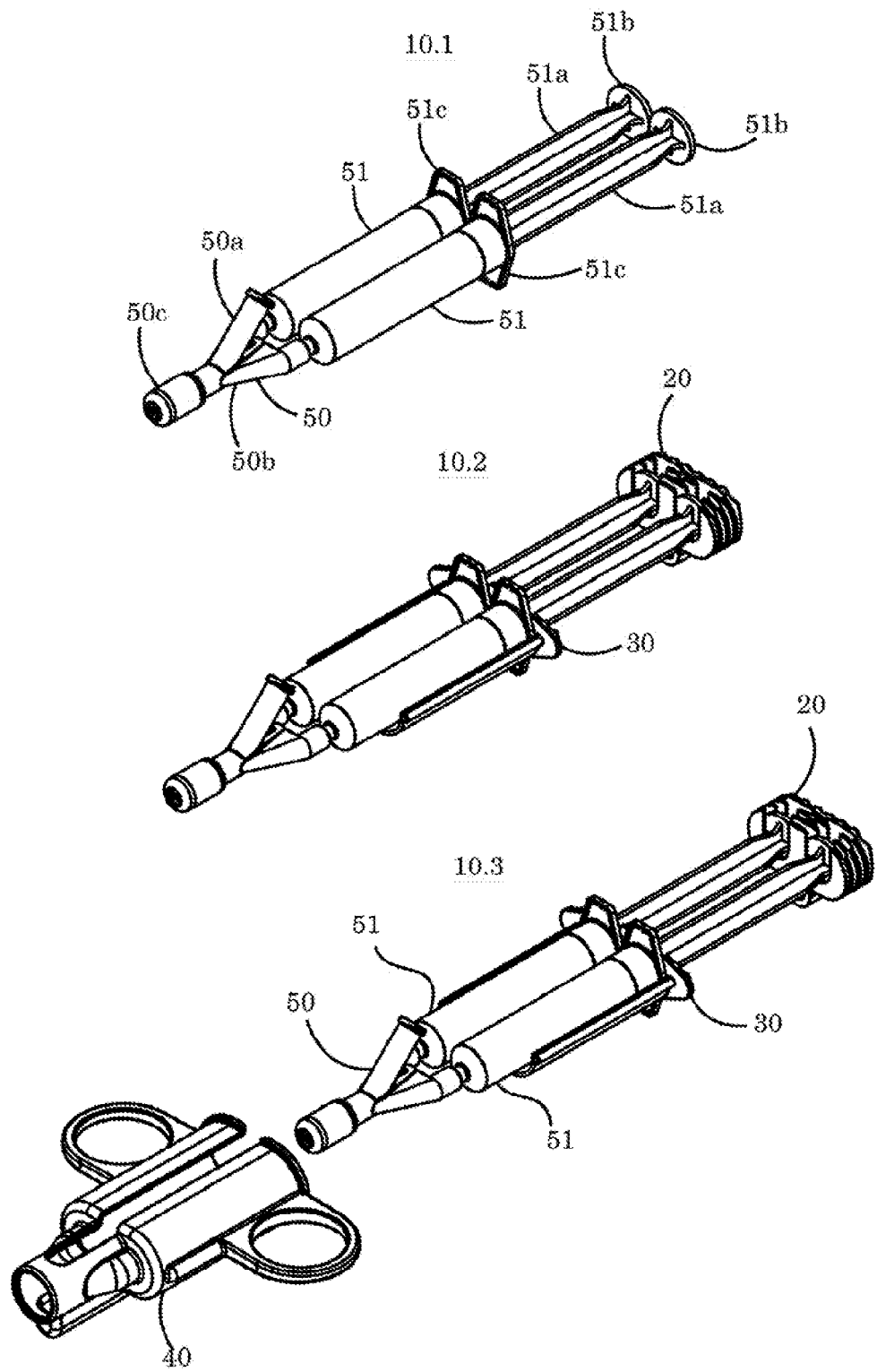
FIG. 8 is an isometric view of the normal progression/method of loading the dual syringes and atomizer spray head into the plunger and cradle components readied for insertion into the holster to complete the final assembly as they would be configured in normal usage of the dual syringe delivery device, all in accordance with the invention.

As shown in FIG. 8, illustrates the method of use for the dual syringe delivery device 10.1 illustrates step one of inserting, the two pre-loaded 5 ml syringes 51 and with the plungers 51a fully extended, into the atomizer spray head 50; 10.2 illustrates step two of loading the two syringes 51 and atomizer spray head 50 into position in the, plunger 20 and cradle 30; 10.3 illustrates step three "the final step" of loading the two syringes 51, atomizer spray head 50, cradle 30 and plunger 20 into the holster 40 and readied for use.

Figure 9:
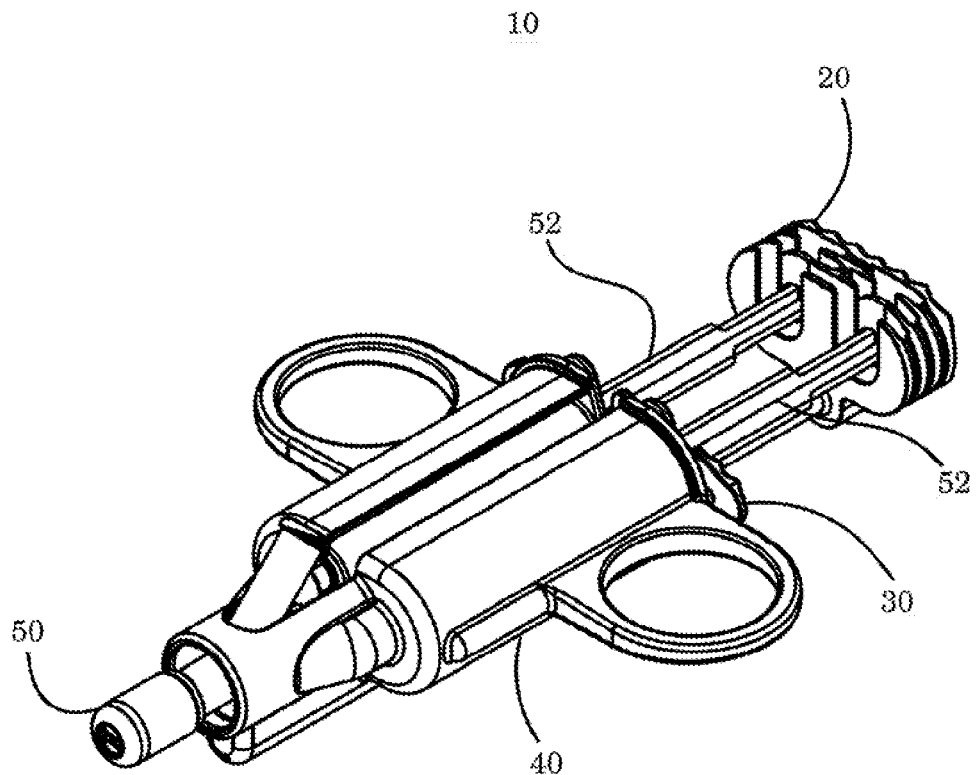
FIG. 9 is an isometric view of the cradle, plunger, and holster components with dual 2 ml syringes and atomizer spray head in final assembly as they would be configured in normal usage of the dual syringe delivery device, all in accordance with the invention.

As shown in FIG. 9, the dual syringe delivery device is illustrated in its final assembled state and configured with 2 ml syringes 52 demonstrating its capability to handle varying hypodermic syringe plunger head sizes and plunger strokes and volume sizes all in accordance with the invention.

Figure 10:
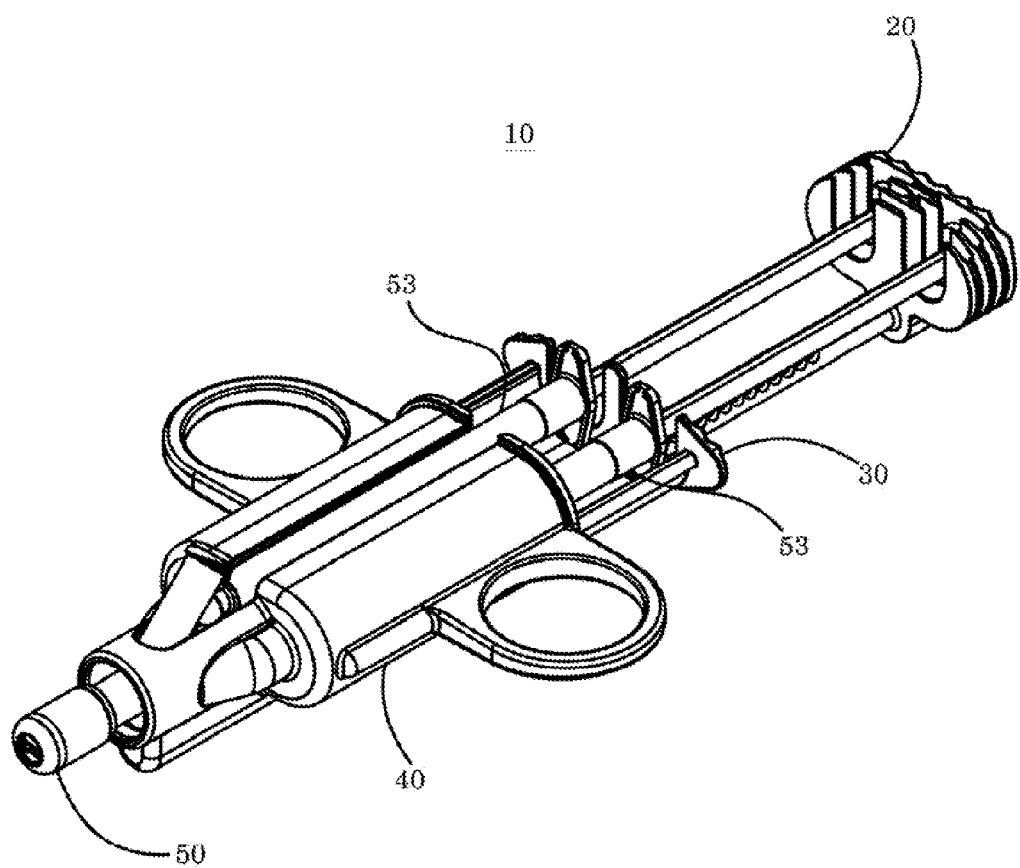
FIG. 10 is an isometric view of the cradle, plunger, and holster components with dual 1 ml syringes and atomizer spray head in final assembly as they would be configured in normal usage of the dual syringe delivery device, all in accordance with the invention.

As shown in FIG. 10, the dual syringe delivery device is illustrated in its final assembled state and configured with 1 ml syringes 53 demonstrating its capability to handle varying hypodermic syringe plunger head sizes and plunger strokes and volume sizes all in accordance with the invention.

Figure 11:
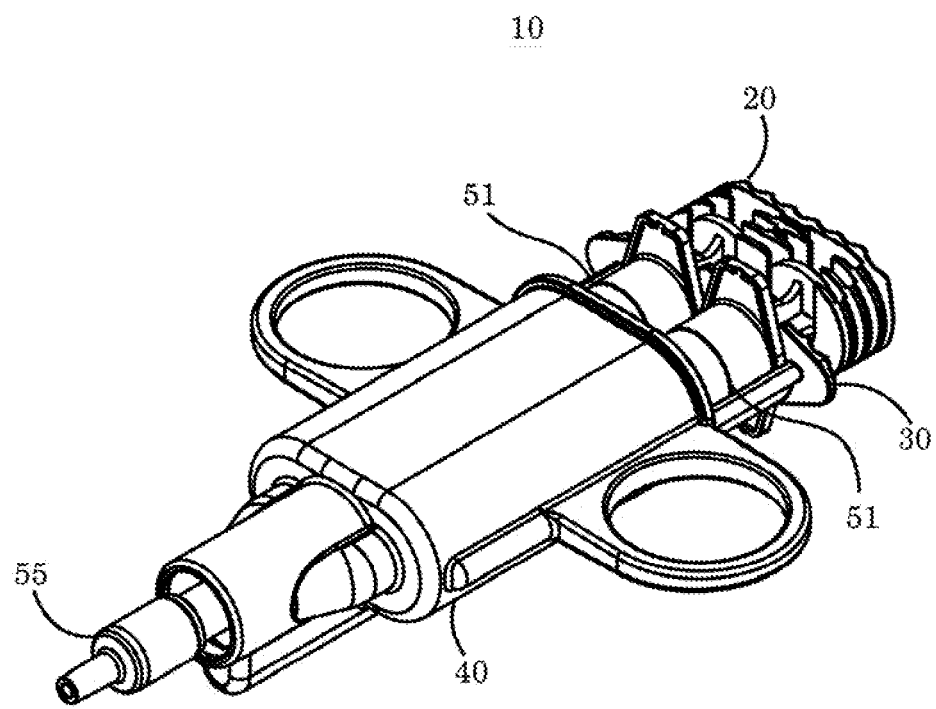
FIG. 11 is an isometric view of the cradle, plunger, and holster components with dual 5 ml syringes and needle head as they would be configured in normal usage of the dual syringe delivery device in an hypodermic needle application, all in accordance with the invention.

As shown in FIG. 11, the dual syringe delivery device is illustrated in its final assembled state and configured with 5 ml syringes 51 and a hypodermic needle fitting tip demonstrating its capability to handle varying tip heads all in accordance with the invention.

In practice, the invention provides a method of dispensing fibrin glues. The method collectively comprised of a plunger, cradle, holster, atomizer spray head which accepts standard air/gas sources and solution delivery systems e.g. syringes.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application, was specifically and individually indicated by reference. In case of conflict between the present disclosure and the incorporated patents, publications and references, the present disclosure should control.

The invention claimed is:

1. A dual syringe delivery device with capability to handle varying hypodermic syringe plunger head sizes, plunger strokes and volume collectively comprising:
a plunger;
a cradle;
a holster;
said plunger having a proximal head and a distally extending cylindrical shaft which joins with an aperture in the cradle,
said cradle having a proximal flange and a distally extending body which joins with an aperture of the holster,
said holster having a body, said body having an interior surface and an exterior surface and an interior aperture, said body having a contoured distal nose area to receive a spray head, said body having a protrusion at the proximal end of said body which extends upward and around said exterior surface of said holster,
said plunger joined to said cradle then joined with said holster so that joined said plunger and said cradle are situated in the interior aperture of said holster.

2. The plunger of claim 1, wherein the head having a plurality of horizontal slots laying perpendicular to the longitudinal axis and proportioned to accept standard hypodermic syringe plunger heads of 1 ml, 2 ml, and 5 ml syringes.

3. The plunger of claim 1, wherein the head having a plurality of horizontal slots laying perpendicular to the longitudinal axis and positioned, 1 ml most proximal, 2 ml central, 5 ml most distal, to accommodate stroke requirements of standard hypodermic syringe plunger of 1 ml, 2 ml, and 5 ml syringes.

4. The plunger of claim 1, wherein the head having two longitudinal U shaped apertures either side of the longitudinal centerline and proportioned to accept standard hypodermic syringe plunger shaft.

5. The plunger of claim 1, wherein the head having a series of raised protrusion on the proximal surface providing grip.

6. The plunger of claim 1, wherein the shaft has an anti-rotating concave surface extending from the distal tip of the shaft to the distal surface of the head.

7. The plunger of claim 1, wherein the cylindrical shall having a series of static positioning grooves lying perpendicular to the longitudinal centerline.

8. The cradle of claim 1, wherein the flange having two longitudinal U shaped apertures either side of the longitudinal centerline and proportioned to accept standard hypodermic syringe plunger shaft.

9. The cradle of claim 1, wherein the flange having a series of raised elements on the proximal surface located at its outer extent about the longitudinal centerline which provide gripping.

10. The cradle of claim 1, wherein the body having a longitudinal first and second rail on the outer edges of the body and proportioned to join with two channels on the holster.

11. The cradle of claim 8, wherein the distally extending body having two apertures either side of the longitudinal centerline positioned against the flange distal surface and adjacent to the U shaped apertures and proportioned to accept standard hypodermic syringe body finger tab.

12. The cradle of claim 1, wherein the body having a tubular protrusion along the longitudinal centerline with an aperture having a convex surface proportioned to join with the concave surface of the shaft of the plunger.

13. The cradle of claim 12, wherein the tubular protrusion having a series of static positioning grooves facing in the direction opposite the body and lying perpendicular to the longitudinal centerline.

14. The cradle of claim 12, wherein the body having static positioning detent tab with pawl positioned on the longitudinal centerline of the tubular protrusion.

15. The holster of claim 1, wherein the body having a first finger loop aperture and a second finger loop aperture either side of the longitudinal centerline.

16. The holster of claim 10, wherein the body having a longitudinal U shaped first channel and second channel on the interior of the body proportioned to allow passage of the rail set located on the outer extent of the cradle body.

17. The holster of claim 12, wherein the body having a U shaped channel located on the inner surface and positioned along the longitudinal centerline which extends from the most proximal surface on the flange distally to the distal nose area and proportioned to join with the tubular protrusion located on the longitudinal centerline and exterior surface of the cradle.

18. The holster of claim 17, wherein the body having a retention tab with pawl centered on the longitudinal centerline and U shaped channel of the body.

19. The holster of claim 1, wherein having a distal nose area of the body having an aperture in the most distal tip which is proportioned to allow passage of a spray head tip the distal nose area is contoured to mirror the contours of the spray head, the contours act as a physical stop against the spray head when the device is fully assembled with the spray head seated in the device.

* * * * *